(12) United States Patent
Lagrange et al.

(10) Patent No.: US 7,329,289 B2
(45) Date of Patent: Feb. 12, 2008

(54) USE OF TRIARYLMETHANE DERIVATIVES AS DIRECT DYES IN A DYE COMPOSITION, COMPOSITION AND IMPLEMENTATION PROCESS

(75) Inventors: Alain Lagrange, Coupvray (FR); Frédéric Guerin, Paris (FR)

(73) Assignee: L'Oréal, S.A., Paris (FR)

( * ) Notice: Subject to any disclaimer, the term of this patent is extended or adjusted under 35 U.S.C. 154(b) by 289 days.

(21) Appl. No.: 11/141,204

(22) Filed: Jun. 1, 2005

(65) Prior Publication Data

US 2006/0021161 A1   Feb. 2, 2006

(30) Foreign Application Priority Data

Jun. 1, 2004 (FR) .................................. 04 05888

(51) Int. Cl.
*A61K 7/13* (2006.01)
(52) U.S. Cl. ...................... 8/405; 8/426; 8/435; 8/643; 8/648; 132/202; 132/208
(58) Field of Classification Search .................... 8/405, 8/426, 435, 643, 648; 132/202, 208
See application file for complete search history.

(56) References Cited

U.S. PATENT DOCUMENTS

| | | | |
|---|---|---|---|
| 4,003,699 A | 1/1977 | Rose et al. | |
| 4,823,985 A | 4/1989 | Grollier et al. | |
| 5,061,289 A | 10/1991 | Clausen et al. | |
| 5,380,340 A | 1/1995 | Neunhoeffer et al. | |
| 5,534,267 A | 7/1996 | Neunhoeffer et al. | |
| 5,663,366 A | 9/1997 | Neunhoeffer et al. | |
| 5,708,151 A | 1/1998 | Möckli | |
| 5,766,576 A | 6/1998 | Löwe et al. | |
| 6,099,592 A | 8/2000 | Vidal et al. | |
| 6,284,003 B1 | 9/2001 | Rose et al. | |
| 6,338,741 B1 | 1/2002 | Vidal et al. | |
| 6,645,258 B2 | 11/2003 | Vidal et al. | |
| 6,730,789 B1 | 5/2004 | Birault et al. | |
| 6,828,159 B1 * | 12/2004 | Drexhage et al. | 436/546 |
| 6,849,315 B2 | 2/2005 | Lehmann et al. | |
| 2002/0050013 A1 | 5/2002 | Vidal et al. | |
| 2003/0019051 A9 | 1/2003 | Vidal et al. | |
| 2004/0142137 A1 | 7/2004 | Lehmann et al. | |

FOREIGN PATENT DOCUMENTS

| | | |
|---|---|---|
| DE | 23 59 399 A1 | 6/1975 |
| DE | 38 43 892 A1 | 6/1990 |
| DE | 41 33 957 A1 | 4/1993 |
| DE | 195 43 988 A1 | 5/1997 |
| EP | 0 714 954 B1 | 6/1996 |
| EP | 0 770 375 B1 | 5/1997 |
| FR | 2 586 913 A1 | 3/1987 |
| FR | 2 733 749 A1 | 11/1996 |
| FR | 2 801 308 A1 | 5/2001 |
| GB | 1 026 978 | 4/1966 |
| GB | 1 153 196 | 5/1969 |
| JP | 20-19576 | 1/1990 |
| JP | 5-163124 | 6/1993 |
| WO | WO 94/08969 | 4/1994 |
| WO | WO 94/08970 | 4/1994 |
| WO | WO 95/01772 | 1/1995 |
| WO | WO 95/15144 | 6/1995 |
| WO | WO 96/15765 | 5/1996 |
| WO | WO 00/64986 | * 11/2000 |
| WO | WO 03/007296 A1 | 1/2003 |

OTHER PUBLICATIONS

STIC Search Report dated on Apr. 16, 2007.*
French Search Report for FR 0405888 (French priority application for the present application), dated Dec. 21, 2004.
English language abstract of EP 0 770 375 B1, May 2, 1997.
English language abstract of JP 20-19576, Jan. 23, 1990.
English language abstract of JP 5-163124, Jun. 29, 1993.

* cited by examiner

*Primary Examiner*—Eisa Elhilo
(74) *Attorney, Agent, or Firm*—Finnegan, Henderson, Farabow, Garrett & Dunner, LLP

(57) ABSTRACT

The present patent application relates to the use of triarylmethane derivatives as direct dyes in a dye composition for keratin fibres, in particular human keratin fibres such as the hair, or for the manufacture of such compositions.

The present patent application also relates to a dye composition for dyeing keratin fibres, in particular human keratin fibres such as the hair, comprising, in a suitable dyeing medium, at least one particular triarylmethane-based direct dye.

The present patent application also relates to a process for dyeing keratin fibres, in particular human keratin fibres such as the hair, using the dye composition according to the invention.

48 Claims, No Drawings

USE OF TRIARYLMETHANE DERIVATIVES AS DIRECT DYES IN A DYE COMPOSITION, COMPOSITION AND IMPLEMENTATION PROCESS

The present patent application relates to the use of triarylmethane derivatives as direct dyes in a dye composition for keratin fibres, in particular human keratin fibres such as the hair.

It is known practice to dye keratin fibres, and in particular human hair, with dye compositions containing oxidation dye precursors, which are generally known as oxidation bases, such as ortho- or para-phenylenediamines, ortho- or para-aminophenols, and heterocyclic compounds. These oxidation bases are colourless or weakly coloured compounds that, when combined with oxidizing products, may give rise to coloured compounds by a process of oxidative condensation.

It is also known that the shades obtained with these oxidation bases may be varied by combining them with couplers or coloration modifiers, the latter being chosen especially from aromatic meta-diamines, meta-aminophenols, meta-diphenols and certain heterocyclic compounds such as indole compounds.

The variety of molecules used as oxidation bases and couplers allows a wide range of colours to be obtained.

The "permanent" coloration obtained using these oxidation dyes must moreover satisfy a certain number of requirements. Thus, it must have no toxicological drawback, it must be able to produce shades in the desired intensity, and it must show good resistance to external agents such as light, bad weather, washing, permanent-waving, perspiration and rubbing.

The dyes must also be able to cover grey hair and, finally, they must be as unselective as possible, i.e. they must produce the smallest possible differences in coloration along the same keratin fibre, which is generally differently sensitized (i.e. damaged) between its end and its root.

It is also known practice to dye keratin fibres with a direct or semi-permanent dye. The process conventionally used in direct dyeing consists in applying to the keratin fibres direct dyes, which are coloured and colouring molecules with affinity for the fibres, leaving the coloured molecules on the fibres to allow them to penetrate, by diffusion, into the hair, and then rinsing the fibres.

In contrast with oxidation dye compositions, direct or semi-permanent dye compositions are used without the mandatory presence of an oxidizing agent. These dyeing operations may be performed repeatedly without degrading the keratin fibre.

It is known practice, for example, to use nitrobenzene, anthraquinone, nitropyridine, azo, xanthene, acridine, azine or triarylmethane direct dyes.

This results in colorations that are often chromatic, but which are, however, temporary or semi-permanent on account of the nature of the bonds between the direct dyes and the keratin fibre. These interactions are such that desorption of the dyes from the surface and/or the core of the fibre takes place easily. The colorations generally show low dyeing power and poor fastness with respect to washing or perspiration.

There is a real need for direct dye compositions that are improved in terms of harmlessness, fastness and selectivity, the latter resulting from the difference in uptake between different parts of a hair or of a head of hair.

The Applicant has just discovered, surprisingly and advantageously, that the use of triarylmethane derivatives as direct dyes in compositions for dyeing keratin fibres, in particular human keratin fibres such as the hair, allows these improvements.

Besides their advantage in terms of harmlessness, the compositions comprising these particular triarylmethane derivatives give dyeing results that are resistant to external agents (sunlight and bad weather) and also to shampooing and perspiration.

In addition, these compositions have a good toxicological profile.

A first subject of the present patent application is the use of particular triarylmethane derivatives as direct dyes in a dye composition for keratin fibres, in particular human keratin fibres such as the hair, or for the manufacture of such compositions.

A second subject of the present patent application is an aqueous dye composition for dyeing keratin fibres, in particular human keratin fibres such as the hair, comprising, in a suitable dyeing medium, at least one particular triarylmethane-based direct dye, at least one oxidation base and/or at least one direct dye different from the particular triarylmethane derivative.

A third subject of the present invention is a process for dyeing keratin fibres, in particular human keratin fibres such as the hair, using the dye composition according to the invention.

Another subject of the present patent application is a process for lightening keratin fibres, in particular human keratin fibres such as the hair, using the dye composition according to the invention.

Another subject of the present patent application is the use of the said composition for dyeing keratin fibres, in particular human keratin fibres such as the hair.

Another subject of the present patent application is a device with compartments or "kit" comprising the dye composition according to the present invention.

Another subject of the present invention is an aqueous dye composition for dyeing human keratin fibres, such as the hair, comprising, in a suitable medium, at least one leuco compound, which is a particular triarylmethane-based direct dye precursor, at least one oxidation base and/or at least one direct dye other than the particular triarylmethane derivative.

Another subject of the present invention is a process for dyeing keratin fibres using the composition comprising the leuco compound, which is a particular triarylmethane-based direct dye precursor.

Finally, another subject of the present invention is a device with compartments or "kit" comprising the composition comprising the leuco compound, which is a particular triarylmethane-based direct dye precursor.

Other characteristics, aspects, subjects and advantages of the present invention will emerge even more clearly on reading the description and the example that follows.

The triarylmethane-based direct dyes that may be used in the compositions according to the present invention correspond to the compound of formula (Ia) below:

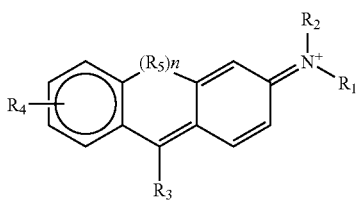

in which:
R$_1$, R$_2$ and R$_3$ represent, independently of each other, a hydrogen atom, a linear or branched, substituted or unsubstituted C$_1$-C$_{24}$ alkyl or C$_2$-C$_{24}$ alkenyl or alkynyl radical, a substituted or unsubstituted benzyl radical, a substituted or unsubstituted aryl radical or an aromatic or nonaromatic, substituted or unsubstituted heterocycle radical, R$_4$ represents a hydrogen atom or a substituted or unsubstituted amino radical, R$_5$ represents a group —CR$_6$R$_7$— in which R$_6$ and R$_7$ represent, independently of each other, a hydrogen atom, a linear or branched, substituted or unsubstituted C$_1$-C$_{24}$ alkyl radical, which can cyclize, a substituted or unsubstituted benzyl radical or a substituted or unsubstituted aryl radical, n denotes 0 or 1, the derivative of formula (Ia) possibly bearing at least one other substituent, which may preferably be chosen from a linear or branched C$_1$-C$_6$ alkyl radical, a linear or branched C$_1$-C$_6$ alkoxy radical, an aryl radical, a halogen atom, especially chlorine, or a nitro group.

The invention also covers the mesomeric forms of the compounds of formula (Ia).

In the context of the definitions of the groups R$_1$, R$_2$, R$_3$, R$_6$ and/or R$_7$, the term "substituted" means substituted with the substituent(s) which may be chosen from a linear or branched C$_1$-C$_6$ alkyl group, except when the groups R$_1$, R$_2$, R$_3$, R$_6$ and/or R$_7$ bearing the substituent represent alkyl, alkenyl or alkynyl groups; a linear or branched C$_1$-C$_6$ hydroxyalkyl group, except when the groups R$_1$, R$_2$, R$_3$, R$_6$ and/or R$_7$ bearing the substituent represent alkyl, alkenyl or alkynyl groups; an acetylamino group; a linear or branched C$_1$-C$_6$ alkylcarbonyl group; a linear or branched C$_1$-C$_6$ alkoxy group; a hydroxycarbonyl group; a linear or branched C$_1$-C$_6$ alkoxycarbonyl group; a hydroxyl group; an amino group; a mono- or dialkylamino group; a mono- or dihydroxyalkylamino group, a nitro group, a halogen atom; an aryl group, an aromatic or non-aromatic heterocycle, these cyclic groups being unsubstituted or substituted with the substituents mentioned above.

Preferably, when these cyclic groups are substituted, the substituent(s) is(are) chosen especially from a hydroxyl group, a C$_1$-C$_6$ alkoxy group, an amino group, a nitro group and/or a halogen atom.

Preferably, when these cyclic groups represent aromatic or non-aromatic heterocycles, they are unsubstituted.

When R$_3$ represents a substituted or unsubstituted aryl radical, the aryl radical may or may not be fused. The aryl radical may thus represent a naphthalene radical.

When R$_3$ represents a substituted or unsubstituted aromatic or non-aromatic heterocycle, the heterocycle may or may not be fused, and may thus represent an indole radical.

The electrical neutrality of the compound of formula (Ia) may be ensured with a counterion Y, the chemical nature of which is not critical.

The counterion Y may be chosen from a cosmetically acceptable anion or mixture of anions. Preferably, the counterion Y is chosen from halides, such as chlorides, bromides, fluorides and iodides; hydroxides; sulfates; hydrogen sulfates; (C$_1$-C$_6$)alkyl sulfates; phosphates; carbonates; hydrogen carbonates; perchlorates; acetates; tartrates; citrates; oxalates; (C$_1$-C$_6$)alkylsulfonates such as methylsulfonate; arylsulfonates, unsubstituted or substituted with a C$_1$-C$_4$ alkyl radical, for instance a 4-tolylsulfonate.

Preferably, the compounds of formula (Ia) that may be used in the compositions according to the present invention are such that R$_1$ and R$_2$ represent, independently of each other, a hydrogen atom, a C$_1$-C$_6$ alkyl radical or a C$_1$-C$_6$ mono- or polyhydroxyalkyl radical.

Preferably, the compounds of formula (Ia) that may be used in the compositions according to the present invention are such that R$_3$ represents a hydrogen atom or an aryl radical optionally substituted with an amino, dialkylamino or dihydroxyalkylamino group.

Preferably, n denotes 1 and R$_5$ preferably denotes the divalent group CR$_6$R$_7$, R$_6$ and R$_7$ denoting a C$_1$-C$_4$ alkyl optionally substituted with one or more halogen atoms.

Preferably, the compounds of formula (Ia) comprise 2 other substituents borne on the tricycle.

As examples of compounds of formula (Ia) that may be used according to the invention, mention may be made of the following compounds:

| Structure | Dye name |
|---|---|
| 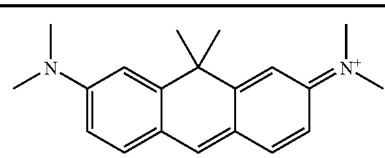 | (7-Dimethylamino-9,9-dimethyl-9H-anthracen-2-ylidene)-dimethylammonium |
| 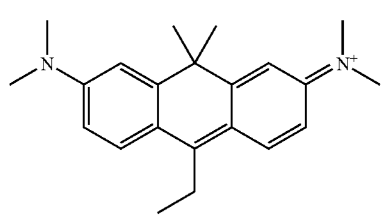 | [7-Dimethylamino-10-ethyl-9,9-dimethyl-9H-anthracen-2-ylidene]dimethylammonium |

-continued

| Structure | Dye name |
|---|---|
| | [7-Dimethylamino-10-(4-dimethyl-aminophenyl)-9,9-dimethyl-9H-anthracen-2-ylidene]dimethyl-ammonium |
| | [7-Diethylamino-10-(4-diethylamino-phenyl)-9,9-dimethyl-9H-anthracen-2-ylidene]dimethylammonium |
| 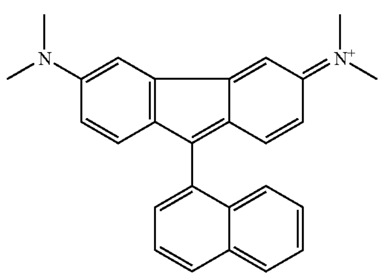 | Methanaminium, N-[6-(dimethylamino)-9-(1-naphthalenyl)-3H-fluoren-3-ylidene]-N-methyl |
| 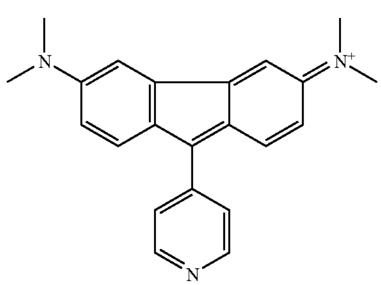 | Methanaminium, N-[6-(dimethylamino)-9-(4-pyridyl)-3H-fluoren-3-ylidene]-N-methyl |

-continued
| Structure | Dye name |
|---|---|
| 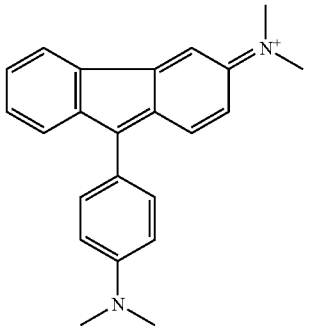 | Methanaminium, N-[9-[4-(dimethylamino)phenyl]-3H-fluoren-3-ylidene]-N-methyl |
| 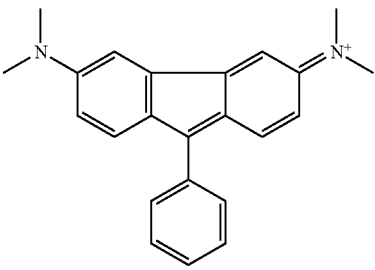 | Bis[3,6-bis(dimethylamino)-9-phenylfluoren-9-ylium] |
| 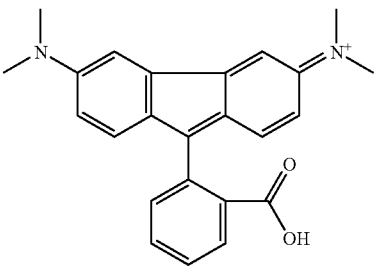 | Benzoic acid, 2-[3,6-bis(dimethylamino)-9H-fluoren-9-ylium] |
| 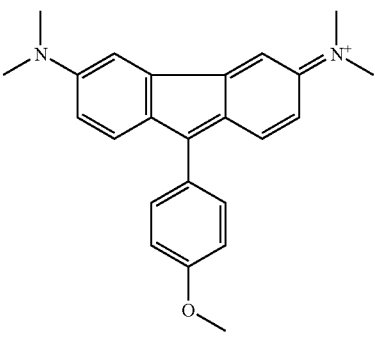 | 3,6-Bis(dimethylamino)-9-(p-methoxyphenyl)fluoren-9-ylium |
| 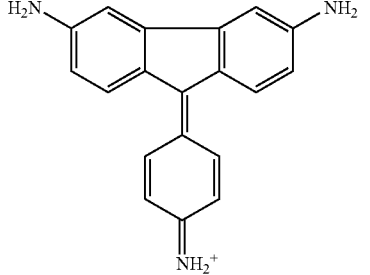 | 4-(3,6-Diaminofluoren-9-ylidene)-cyclohexa-2,5-dienylideneammonium |

-continued

| Structure | Dye name |
|---|---|
| 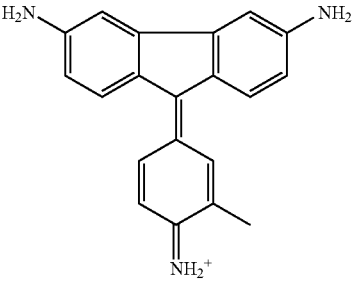 | [4-(3,6-Bis-aminofluoren-9-ylidene)-2-methylcyclohexa-2,5-dienylidene]ammonium |
| 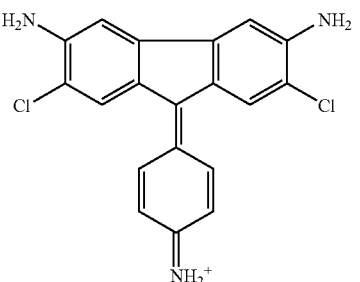 | [4-(3,6-Bis-amino-2,7-dichlorofluoren-9-ylidene)cyclohexa-2,5-dienylidene]ammonium |
| 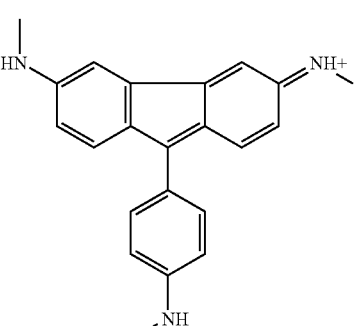 | 9H-Fluorene-3,6-diamine, N,N'-dimethyl-9-[4-(methylamino)phenyl] |
| 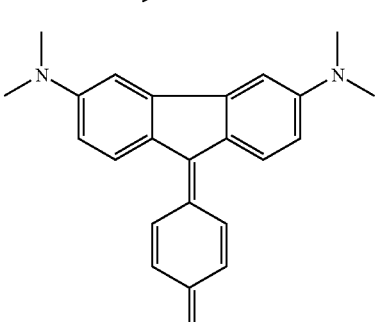 | [4-(3,6-Bis-dimethylaminofluoren-9-ylidene)cyclohexa-2,5-dienylidene]methylammonium |
| 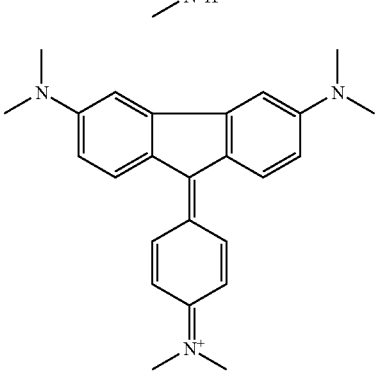 | [4-(3,6-Bis-dimethylaminofluoren-9-ylidene)cyclohexa-2,5-dienylidene]dimethylammonium |

-continued

| Structure | Dye name |
|---|---|
| 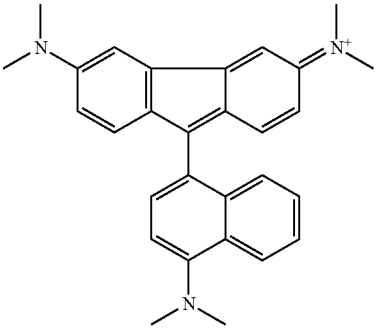 | Methanaminium, N-[6-(dimethylamino)-9-[4-(dimethylamino)-1-naphthalenyl]-3H-fluoren-3-ylidene]-N-methyl |
| 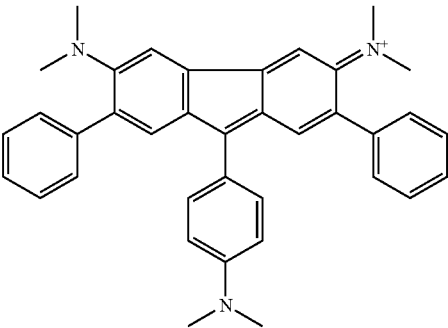 | Methanaminium, N-[6-(dimethylamino)-9-[4-(dimethylamino)phenyl]-2,7-diphenyl-3H-fluoren-3-ylidene]-N-methyl |
| 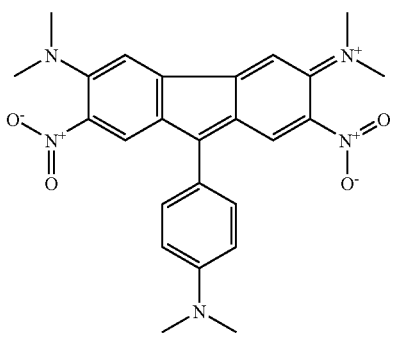 | Methanaminium, N-[6-(dimethylamino)-9-[4-(dimethylamino)phenyl]-2,7-dinitro-3H-fluoren-3-ylidene]-N-methyl |
| 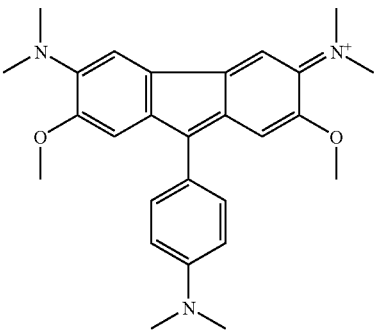 | Methanaminium, N-[6-(dimethylamino)-9-[4-(dimethylamino)phenyl]-2,7-dimethoxy-3H-fluoren-3-ylidene]-N-methyl |

-continued

| Structure | Dye name |
|---|---|
| 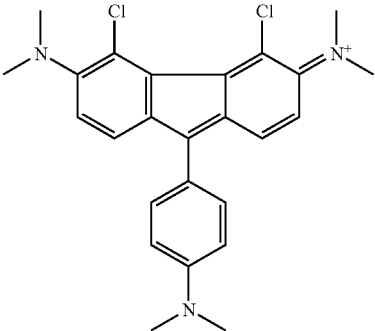 | Methanaminium, N-[4,5-dichloro-6-(dimethylamino)-9-[4-(dimethylamino)phenyl]-3H-fluoren-3-ylidene]-N-methyl |
| 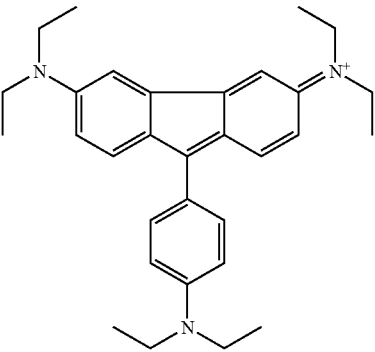 | [4-(3,6-Bis-diethylaminofluoren-9-ylidene)cyclohexa-2,5-dienylidene]diethylammonium |
| 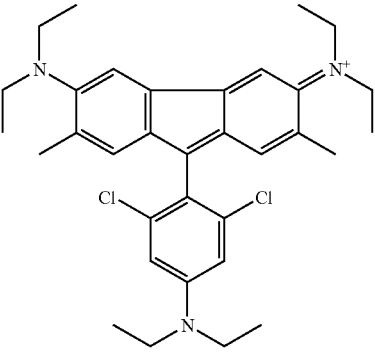 | Ethanaminium, N-[9-[2,6-dichloro-4-(diethylamino)phenyl]-6-(diethylamino)-2,7-dimethyl-3H-fluoren-3-ylidene]-N-ethyl |
| 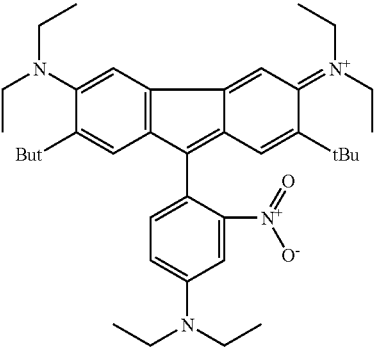 | Ethanaminium, N-[6-(diethylamino)-9-[4-(diethylamino)-2-nitrophenyl]-2,7-bis(1,1-dimethylethyl)-3H-fluoren-3-ylidene]-N-ethyl |

-continued
| Structure | Dye name |
|---|---|
| 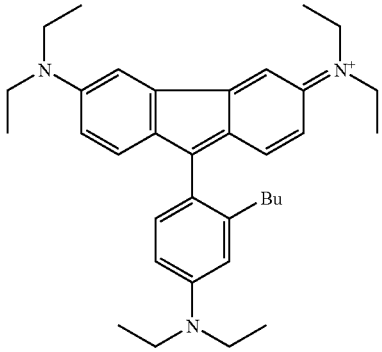 | Ethanaminium, N-[9-[2-butyl-4-(diethylamino)phenyl]-6-(diethylamino)-3H-fluoren-3-ylidene]-N-ethyl |
| 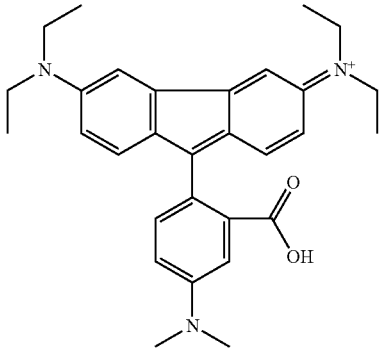 | Benzoic acid, 2-[3,6-bis(diethylamino)-9H-fluoren-9-yl]-5-(dimethylamino) |
| 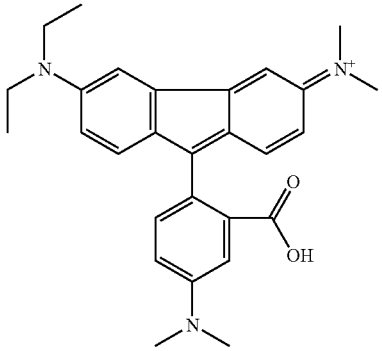 | Benzoic acid, 2-[3-(diethylamino)-6-(dimethylamino)-9H-fluoren-9-yl]-5-(dimethylamino) |
| 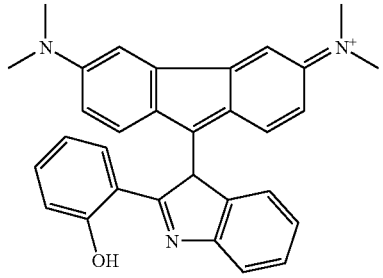 | Phenol, 2-[3-[3,6-bis(dimethylamino)-9H-fluoren-9-ylidene]-3H-indol-2-yl] |

-continued

| Structure | Dye name |
|---|---|
| 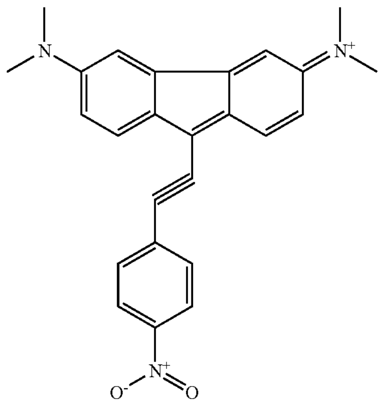 | Methanaminium, N-[6-(dimethylamino)-9-[(4-nitrophenyl)ethynyl]-3H-fluoren-3-ylidene]-N-methyl |
| | Methanaminium, N-[9-[(4-bromophenyl)ethynyl]-6-(dimethylamino)-3H-fluoren-3-ylidene]-N-methyl |
| 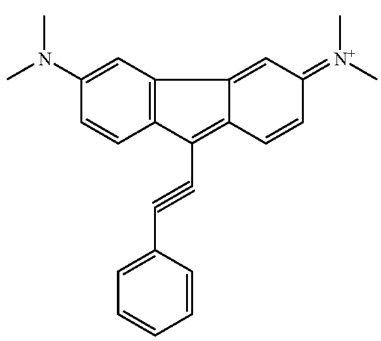 | Methanaminium, N-[6-dimethylamino)-9-(phenylethynyl)-3H-fluoren-3-ylidene]-N-methyl |
| 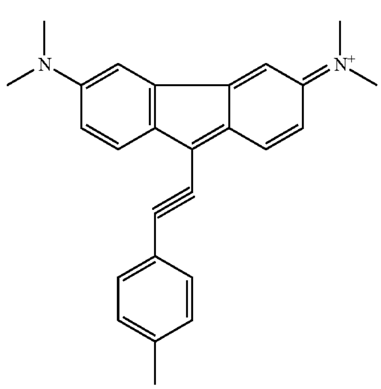 | Methanaminium, N-[6-dimethylamino)-9-[(4-methylphenyl)ethynyl]-3H-fluoren-3-ylidene]-N-methyl |

-continued

| Structure | Dye name |
|---|---|
| 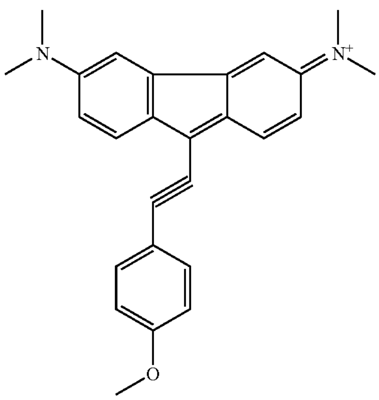 | Methanaminium, N-[6-dimethylamino)-9-[(4-methoxyphenyl)ethynyl]-3H-fluoren-3-ylidene]-N-methyl |
| 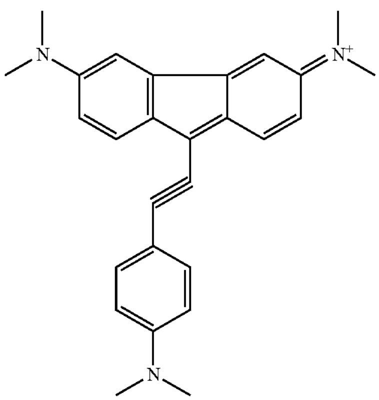 | Methanaminium, N-[6-dimethylamino)-9-[[4-(dimethylamino)phenyl]ethynyl]-3H-fluoren-3-ylidene]-N-methyl |

The compositions used according to the present invention may comprise from 0.001% to 20%, preferably from 0.01% to 10% and more particularly from 0.1% to 5% by weight of triarylmethane-based direct dye(s) of formula (Ia) relative to the total weight of the composition.

The invention also relates to an aqueous dye composition for dyeing keratin fibres, in particular human keratin fibres such as the hair, comprising, in a suitable dyeing medium:
- at least one triarylmethane-based direct dye as defined above,
- at least one oxidation base and/or
- at least one direct dye other than the triarylmethane-based derivative defined above.

The dye composition according to the invention may comprise from 0.001% to 20% and preferably from 0.01% to 10% by weight of triarylmethane-based direct dye(s) of formula (Ia) relative to the total weight of the composition.

The composition of the present invention may also comprise at least one oxidation base.

By way of example, the oxidation bases are chosen from phenylenediamines, bis(phenyl)alkylenediamines, para-aminophenols, ortho-aminophenols and heterocyclic bases, and the addition salts thereof.

Among the para-phenylenediamines that may be mentioned, for example, are para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene and 3-hydroxy-1-(4'-aminophenyl)pyrrolidine, and the addition salts thereof with an acid.

Among the para-phenylenediamines mentioned above, para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloropara-phenylenediamine and 2-β-acetylaminoethyloxy-para-phenylenediamine, and the addition salts thereof with an acid, are particularly preferred.

Among the bis(phenyl)alkylenediamines that may be mentioned, for example, are N,N'-bis(β-hydroxyethyl)-N, N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine and 1,8-bis(2,5-diaminophenoxy)-3,6-dioxaoctane, and the addition salts thereof.

Among the para-aminophenols that may be mentioned, for example, are para-aminophenol, 4-amino-3-methylphenol, 4-amino-3-fluorophenol, 4-amino-3-chlorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the addition salts thereof with an acid.

Among the ortho-aminophenols that may be mentioned, for example, are 2-aminophenol, 2-amino-5-methylphenol, 2-amino-6-methylphenol and 5-acetamido-2-aminophenol, and the addition salts thereof.

Among the heterocyclic bases that may be mentioned, for example, are pyridine derivatives, pyrimidine derivatives and pyrazole derivatives.

Among the pyridine derivatives that may be mentioned are the compounds described, for example, in patents GB 1 026 978 and GB 1 153 196, for instance 2,5-diaminopyridine, 2-(4-methoxyphenyl)amino-3-aminopyridine, and 3,4-diaminopyridine, and the addition salts thereof.

Other pyridine oxidation bases that are useful in the present invention are the 3-aminopyrazolo[1,5-a]pyridine oxidation bases or addition salts thereof described, for example, in patent application FR 2 801 308. Examples that may be mentioned include pyrazolo-[1,5-a]pyrid-3-ylamine, 2-acetylaminopyrazolo[1,5-a]pyrid-3-ylamine, 2-morpholin-4-ylpyrazolo[1,5-a]pyrid-3-ylamine, 3-aminopyrazolo-[1,5-a]pyridine-2-carboxylic acid, 2-methoxypyrazolo[1,5-a]pyrid-3-ylamino, (3-aminopyrazolo[1,5-a]pyrid-7-yl)methanol, 2-(3-aminopyrazolo[1,5-a]pyrid-5-yl)ethanol, 2-(3-aminopyrazolo[1,5-a]pyrid-7-yl)ethanol, (3-aminopyrazolo[1,5-a]pyrid-2-yl)methanol, 3,6-diaminopyrazolo[1,5-a]pyridine, 3,4-diaminopyrazolo[1,5-a]pyridine, pyrazolo-[1,5-a]pyridine-3,7-diamine, 7-morpholin-4-ylpyrazolo[1,5-a]pyrid-3-ylamine, pyrazolo[1,5-a]pyridine-3,5-diamine, 5-morpholin-4-ylpyrazolo[1,5-a]pyrid-3-ylamine, 2-[(3-aminopyrazolo[1,5-a]pyrid-5-yl)-(2-hydroxyethyl)amino]ethanol, 2-[(3-aminopyrazolo[1,5-a]pyrid-7-yl)-(2-hydroxyethyl)amino]ethanol, 3-aminopyrazolo[1,5-a]pyridin-5-ol, 3-aminopyrazolo[1,5-a]pyridin-4-ol, 3-aminopyrazolo[1,5-a]pyridin-6-ol and 3-aminopyrazolo[1,5-a]pyridin-7-ol,
and the addition salts thereof.

Among the pyrimidine derivatives that may be mentioned are the compounds described, for example, in patents DE 2 359 399; JP 88-169 571; JP 05-63124; EP 0 770 375 or patent application WO 96/15765, for instance 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine and 2,5,6-triaminopyrimidine, and the addition salts thereof, and the tautomeric forms thereof, when a tautomeric equilibrium exists.

Among the pyrazole derivatives that may be mentioned are the compounds described in patents DE 3 843 892 and DE 4 133 957, and patent applications WO 94/08969, WO 94/08970, FR-A-2 733 749 and DE 195 43 988, for instance 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole and 3,5-diamino-4-(β-hydroxyethyl)amino-1-methylpyrazole, and the addition salts thereof. 4,5-Diamino-1-(β-methoxyethyl)pyrazole may also be used.

The oxidation base(s) present in the composition of the invention is (are) generally present in an amount of between 0.001% and 20% by weight approximately, and preferably between 0.005% and 6%, relative to the total weight of the dye composition.

The dye composition in accordance with the invention may also contain one or more additional direct dyes other than the triarylmethane-based direct dyes of formula (Ia), which may especially be chosen from neutral, acidic or cationic nitrobenzene dyes, neutral, acidic or cationic azo direct dyes, neutral, acidic or cationic quinone and in particular anthraquinone direct dyes, azine direct dyes, triarylmethane direct dyes, indoamine direct dyes and natural direct dyes.

Among the benzene-based direct dyes that may be used according to the invention, mention may be made, in a non-limiting manner, of the following compounds:
  1,4-diamino-2-nitrobenzene
  1-amino-2-nitro-4-(β-hydroxyethylamino)benzene
  1-amino-2-nitro-4-bis(β-hydroxyethyl)aminobenzene
  1,4-bis(β-hydroxyethylamino)-2-nitrobenzene
  1-β-hydroxyethylamino-2-nitro-4-bis(β-hydroxyethylamino)-benzene
  1-β-hydroxyethylamino-2-nitro-4-aminobenzene
  1-β-hydroxyethylamino-2-nitro-4-(ethyl)(β-hydroxyethyl)aminobenzene
  1-amino-3-methyl-4-β-hydroxyethylamino-6-nitrobenzene
  1-amino-2-nitro-4-β-hydroxyethylamino-5-chlorobenzene
  1,2-diamino-4-nitrobenzene
  1-amino-2-β-hydroxyethylamino-5-nitrobenzene
  1,2-bis(β-hydroxyethylamino)-4-nitrobenzene
  1-amino-2-[tris(hydroxymethyl)methylamino]-5-nitrobenzene
  1-hydroxy-2-amino-5-nitrobenzene
  1-hydroxy-2-amino-4-nitrobenzene
  1-hydroxy-3-nitro-4-aminobenzene
  1-hydroxy-2-amino-4,6-dinitrobenzene
  1-β-hydroxyethyloxy-2-β-hydroxyethylamino-5-nitrobenzene
  1-methoxy-2-β-hydroxyethylamino-5-nitrobenzene
  1-β-hydroxyethyloxy-3-methylamino-4-nitrobenzene
  1-β,γ-dihydroxypropyloxy-3-methylamino-4-nitrobenzene
  1-β-hydroxyethylamino-4-β,γ-dihydroxypropyloxy-2-nitrobenzene 1-β,γ-dihydroxypropylamino-4-trifluoromethyl-2-nitrobenzene
1-β-hydroxyethylamino-4-trifluoromethyl-2-nitrobenzene
1-β-hydroxyethylamino-3-methyl-2-nitrobenzene
1-β-aminoethylamino-5-methoxy-2-nitrobenzene
1-hydroxy-2-chloro-6-ethylamino-4-nitrobenzene
1-hydroxy-2-chloro-6-amino-4-nitrobenzene
1-hydroxy-6-[bis(β-hydroxyethyl)amino]-3-nitrobenzene
1-β-hydroxyethylamino-2-nitrobenzene
1-hydroxy-4-β-hydroxyethylamino-3-nitrobenzene.

Among the azo direct dyes that may be used according to the invention, mention may be made of the cationic azo dyes described in patent applications WO 95/15144, WO 95/01772 and EP 714 954, the content of which forms an integral part of the invention.

Among these compounds, mention may be made most particularly of the following dyes:
  1,3-dimethyl-2-[[4-(dimethylamino)phenyl]azo]-1H-imidazolium chloride,
  1,3-dimethyl-2-[(4-aminophenyl)azo]-1H-imidazolium chloride,
  1-methyl-4-[(methylphenylhydrazono)methyl]pyridinium methyl sulfate.

Among the azo direct dyes that may also be mentioned are the following dyes described in the Colour Index International 3rd edition:
  Disperse Red 17
  Acid Yellow 9
  Acid Black 1
  Basic Red 22
  Basic Red 76
  Basic Yellow 57
  Basic Brown 16
  Acid Yellow 36
  Acid Orange 7
  Acid Red 33
  Acid Red 35
  Basic Brown 17
  Acid Yellow 23
  Acid Orange 24
  Disperse Black 9.

Mention may also be made of 1-(4'-aminodiphenylazo)-2-methyl-4-[bis(β-hydroxyethyl)amino]benzene and 4-hydroxy-3-(2-methoxyphenylazo)-1-naphthalenesulfonic acid.

Among the quinone direct dyes that may be mentioned are the following dyes:
  Disperse Red 15
  Solvent Violet 13
  Acid Violet 43
  Disperse Violet 1
  Disperse Violet 4
  Disperse Blue 1
  Disperse Violet 8
  Disperse Blue 3
  Disperse Red 11
  Acid Blue 62
  Disperse Blue 7
  Basic Blue 22
  Disperse Violet 15
  Basic Blue 99
  and also the following compounds:
  1-N-methylmorpholiniumpropylamino-4-hydroxyanthraquinone
  1-aminopropylamino-4-methylaminoanthraquinone
  1-aminopropylaminoanthraquinone
  5-β-hydroxyethyl-1,4-diaminoanthraquinone
  2-aminoethylaminoanthraquinone
  1,4-bis(β,γ-dihydroxypropylamino)anthraquinone.

Among the azine dyes that may be mentioned are the following compounds:
  Basic Blue 17
  Basic Red 2.

Among the triarylmethane dyes that may be used according to the invention, mention may be made of the following compounds:
  Basic Green 1
  Acid Blue 9
  Basic Violet 3
  Basic Violet 14
  Basic Blue 7
  Acid Violet 49
  Basic Blue 26
  Acid Blue 7.

Among the indoamine dyes that may be used according to the invention, mention may be made of the following compounds:
  2-β-hydroxyethylamino-5-[bis(β-4'-hydroxyethyl)amino]anilino-1,4-benzoquinone;
  2-β-hydroxyethylamino-5-(2'-methoxy-4'-amino)anilino-1,4-benzoquinone;
  3-N(2'-chloro-4'-hydroxy)phenylacetylamino-6-methoxy-1,4-benzoquinoneimine;
  3-N(3'-chloro-4'-methylamino)phenylureido-6-methyl-1,4-benzoquinoneimine;
  3-[4'-N-(ethylcarbamylmethyl)amino]phenylureido-6-methyl-1,4-benzoquinoneimine.

Among the natural direct dyes that may be used according to the invention, mention may be made of lawsone, juglone, alizarin, purpurin, carminic acid, kermesic acid, purpurogallin, protocatechaldehyde, indigo, isatin, curcumin, spinulosin and apigenidin. Extracts or decoctions containing these natural dyes may also be used, and especially henna-based poultices or extracts.

The direct dye(s) preferably represent(s) from 0.001% to 20% by weight approximately, and even more preferably from 0.005% to 10% by weight approximately, relative to the total weight of the composition.

If the composition contains at least one oxidation base, the composition according to the invention preferably contains one or more couplers conventionally used for dyeing keratin fibres. Among these couplers, mention may be made especially of meta-phenylenediamines, meta-aminophenols, meta-diphenols, naphthalene-based couplers and heterocyclic couplers, and the addition salts thereof.

Examples that may be mentioned include 1,3-dihydroxybenzene, 1,3-dihydroxy-2-methylbenzene, 4-chloro-1,3-dihydroxybenzene, 2,4-diamino-1-(β-hydroxyethyloxybenzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene and 2,6-bis(β-hydroxyethylamino)toluene, and the addition salts thereof.

In the composition of the present invention, the coupler(s) is (are) generally present in an amount ranging from 0.001% to 20% and preferably ranging from 0.005% to 6% by weight approximately relative to the total weight of the dye composition.

In general, the addition salts of the oxidation bases and couplers that may be used in the context of the invention are chosen especially from the addition salts with an acid, such as the hydrochlorides, hydrobromides, sulfates, citrates, succinates, tartrates, lactates, tosylates, benzenesulfonates, phosphates and acetates, and the addition salts with a base, such as sodium hydroxide, potassium hydroxide, ammonia, amines or alkanolamines.

The composition according to the invention may also comprise at least one oxidizing agent conventionally used for the oxidation dyeing of keratin fibres, such as, for example, hydrogen peroxide, urea peroxide, alkali metal bromates, persalts such as perborates and persulfates, peracids, and oxidase enzymes, among which mention may be made of peroxidases, 2-electron oxidoreductases such as uricases, and 4-electron oxygenases, for instance laccases. Hydrogen peroxide is particularly preferred.

The medium that is suitable for dyeing, also known as the dye support, is a cosmetic medium generally consisting of water or of a mixture of water and of at least one organic solvent to dissolve the compounds that are not sufficiently water-soluble. Examples of organic solvents that may be mentioned include $C_1$-$C_4$ lower alkanols such as ethanol and isopropanol; polyols and polyol ethers, for instance 2-butoxyethanol, propylene glycol, glycerol, propylene glycol monomethyl ether, diethylene glycol monoethyl ether and monomethyl ether, and also aromatic alcohols, for instance benzyl alcohol or phenoxyethanol, and mixtures thereof.

The solvents are preferably present in proportions preferably of between 1% and 40% by weight-approximately and even more preferably between 5% and 30% by weight approximately relative to the total weight of the dye composition.

The dye composition in accordance with the invention may also contain various adjuvants conventionally used in hair dye compositions, such as anionic, cationic, nonionic, amphoteric or zwitterionic surfactants or mixtures thereof, anionic, cationic, nonionic, amphoteric or zwitterionic polymers or mixtures thereof, mineral or organic thickeners, and in particular anionic, cationic, nonionic and amphoteric associative thickeners, antioxidants, penetrating agents, sequestering agents, fragrances, buffers, dispersants, conditioners, for instance volatile or non-volatile, modified or unmodified silicones, film-forming agents, ceramides, preserving agents and opacifiers.

The above adjuvants are generally present in an amount for each of between 0.01% and 20% by weight relative to the weight of the composition.

Needless to say, a person skilled in the art will take care to select this or these optional additional compound(s) such that the advantageous properties intrinsically associated with the dye composition in accordance with the invention are not, or are not substantially, adversely affected by the envisaged addition(s).

The pH of the dye composition in accordance with the invention is generally between 3 and 12, preferably between 5 and 11 and even more particularly from 6 to 8.5. It may be adjusted to the desired value by means of acidifying or basifying agents usually used for dyeing keratin fibres, or alternatively using standard buffer systems.

Among the acidifying agents that may be mentioned, for example, are mineral or organic acids, for instance hydrochloric acid, orthophosphoric acid, sulfuric acid, carboxylic acids, for instance acetic acid, tartaric acid, citric acid or lactic acid, and sulfonic acids.

Among the basifying agents that may be mentioned, for example, are aqueous ammonia, alkaline carbonates, alkanolamines such as monoethanolamine, diethanolamine and triethanolamine and derivatives thereof, sodium hydroxide, potassium hydroxide and the compounds of formula (II) below:

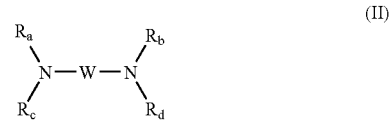

(II)

in which W is a propylene residue optionally substituted with a hydroxyl group or a $C_1$-$C_4$ alkyl radical; $R_a$, $R_b$, $R_c$ and $R_d$, which may be identical or different, represent a hydrogen atom or a $C_1$-$C_4$ alkyl or $C_1$-$C_4$ hydroxyalkyl radical.

The dye composition according to the invention may be in various forms, such as in the form of liquids, creams or gels, or in any other form that is suitable for dyeing keratin fibres, and especially human hair.

The process of the present invention is a process in which the composition according to the present invention as defined above is applied to the keratin fibres, the composition is left on the fibres for a period of between 3 minutes and 1 hour and preferably between 15 minutes and 45 minutes, and the said fibres are then rinsed.

According to one particular embodiment, the composition of the invention, free of oxidizing agent and of oxidation base, is applied to the keratin fibres in the presence of an oxidizing agent for a time sufficient to obtain the desired lightening. The oxidizing agent may be added to the composition of the invention just at the time of use, or it may be used starting with an oxidizing composition containing it, which is applied simultaneously or sequentially to the composition of the invention. After a leave-in time of 3 minutes to 1 hour approximately and preferably of between 15 minutes and 45 minutes, the keratin fibres are rinsed, washed with shampoo, rinsed again and then dried.

According to one particular embodiment, the composition according to the present invention, free of oxidizing agent, comprises at least one oxidation dye precursor, and it is mixed, preferably at the time of use, with a composition containing, in a suitable dyeing medium, at least one oxidizing agent. The oxidizing composition may be applied simultaneously with or sequentially to the composition according to the invention. The mixture obtained is then applied to the keratin fibres. After a leave-in time of 3 minutes to 1 hour approximately and preferably from 15 minutes to 45 minutes approximately, the keratin fibres are rinsed, washed with shampoo, rinsed again and then dried.

The oxidizing composition may also contain various adjuvants conventionally used in hair dye compositions and as defined above.

The pH of the oxidizing composition containing the oxidizing agent is such that, after mixing with the dye composition, the pH of the resulting composition applied to the keratin fibres preferably ranges between 3 and 12 approximately, even more preferably between 5 and 11 and even more particularly between 6 and 8.5. It may be adjusted to the desired value by means of acidifying or basifying agents usually used in the dyeing of keratin fibres and as defined above.

The ready-to-use composition that is finally applied to the keratin fibres may be in various forms, such as in the form of liquids, creams or gels, or in any other form that is suitable for dyeing keratin fibres, and especially human hair.

The invention also relates to the use of the dye composition according to the invention for dyeing keratin fibres.

A subject of the invention is also a multi-compartment device or dyeing "kit", in which a first compartment contains the dye composition according to the invention, free of oxidizing agent and of oxidation base, and a second compartment contains an oxidizing agent. The compartment containing at least one direct dye of formula (Ia) may optionally contain at least one oxidation dye precursor defined above. This device may be equipped with a means for applying the desired mixture to the hair, such as the devices described in patent FR 2 586 913 in the name of the Applicant.

The invention also relates to an aqueous dye composition for dyeing keratin fibres, in particular human keratin fibres such as the hair, comprising, in a suitable dyeing medium:
at least one leuco compound of general formula (Ib), which is a triarylmethane-based direct dye precursor of formula (Ia),

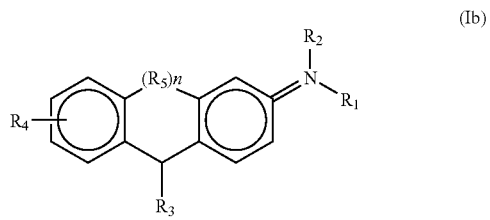

(Ib)

in which $R_1$, $R_2$, $R_3$, $R_4$, $R_5$, $R_6$, $R_7$ and n have the same meaning as in the direct dye of general formula (Ia),
at least one oxidation base and/or
at least one direct dye other than those of formula (Ia).

The dye composition comprising the leuco compound of general formula (Ib) may also comprise all the constituents that are present in the dye composition comprising the triarylmethane-based direct dye of general formula (Ia).

The invention also relates to a process for dyeing keratin fibres, in which the composition comprising the leuco compound of formula (Ib) and a composition comprising an oxidizing agent in order to oxidize the leuco compound of formula (Ib) into a triarylmethane-based direct dye of formula (Ia) is applied to the keratin fibres.

According to one particular embodiment, the composition comprising the leuco compound of formula (Ib), free of oxidizing agent and preferably free of oxidation base, is mixed, preferably at the time of use, with a composition containing, in a suitable dyeing medium, at least one oxidizing agent. The oxidizing composition may be applied simultaneously with or sequentially to the composition comprising the leuco compound of formula (Ib). The mixture obtained is then applied to the keratin fibres. After a leave-in time of 3 minutes to 1 hour approximately and preferably between 15 minutes and 45 minutes, the keratin fibres are rinsed, washed with shampoo, rinsed again and then dried.

The invention also relates to a multi-compartment device or dyeing "kit", in which a first compartment contains the dye composition comprising the leuco compound of formula (Ib), free of oxidizing agent and preferably free of oxidation base, and a second compartment containing an oxidizing agent. The compartment containing at least one direct dye of formula (Ia) may optionally contain at least one oxidation dye precursor defined above. In the same manner as previously, this device may be equipped with a means for applying the desired mixture to the hair, such as the devices described in patent FR-2 586 913 in the name of the Applicant.

The following example serves to illustrate the invention without, however, being limiting in nature.

EXAMPLE

The dye composition below was prepared:

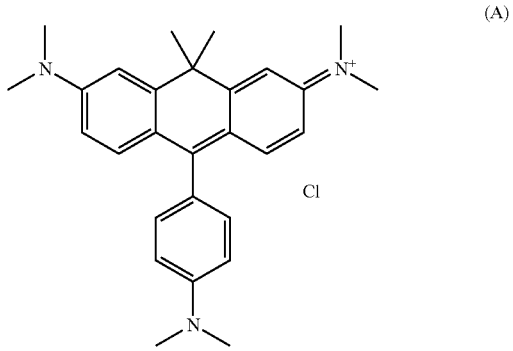

(A)

| Compound | Amount |
|---|---|
| [7-Dimethylamino-10-(4-dimethylaminophenyl)-9,9-dimethyl-9H-anthracen-2-ylidene] chloride | $10^{-3}$ mol % |
| Benzyl alcohol | 4.0 g |
| Polyethylene glycol 6 OE | 6.0 g |
| Hydroxyethylcellulose | 0.7 g |
| Alkylpolyglucoside as an aqueous solution containing 60% AM* | 4.5 g |
| Phosphate buffer | qs pH 7 |
| Demineralized water | qs 100 g |

*Active material

The above composition was applied to locks of natural or permanent-waved grey hair containing 90% white hairs, with a bath ratio of 10, and was left on the hair for 30 minutes at room temperature. After rinsing with running water and drying, the hair was dyed in a blue shade.

What is claimed is:

1. A process for dyeing keratin fibers, comprising applying to the keratin fibers a dyeing composition comprising at least one direct dye chosen from a triarylmethane-based compound of formula (Ia):

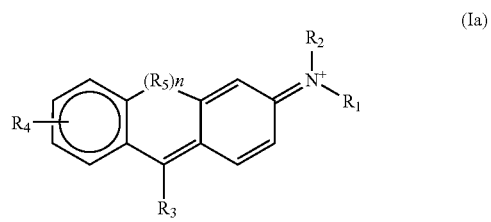

(Ia)

in which:
$R_1$, $R_2$ and $R_3$ are, independently of each other, chosen from a hydrogen atom, a linear or branched, substituted or unsubstituted $C_1$-$C_{24}$ alkyl or $C_2$-$C_{24}$ alkenyl or alkynyl radical, a substituted or unsubstituted benzyl radical, a substituted or unsubstituted aryl radical or an aromatic or nonaromatic, and a substituted or unsubstituted heterocycle radical;

R$_4$ is chosen from a hydrogen atom and a substituted or unsubstituted amino group;

R$_5$ is a group —CR$_6$R$_7$— in which R$_6$ and R$_7$ are, independently of each other, chosen from a hydrogen atom, a linear or branched, substituted or unsubstituted C$_1$-C$_{24}$ alkyl radical, which can cyclize, a substituted or unsubstituted benzyl radical and a substituted or unsubstituted aryl radical;

n is chosen from 0 and 1; and the dye of formula (Ia) optionally having at least one other substituent, a radical being said to be substituted when it bears at least one group chosen from:

- a linear or branched C$_1$-C$_6$ alkyl group, except when the groups R$_1$, R$_2$, R$_3$, R$_6$, and/or R$_7$ bearing the substituent represent alkyl, alkenyl or alkynyl groups;
- a linear or branched C$_1$-C$_6$ hydroxyalkyl group, except when the groups R$_1$, R$_2$, R$_3$, R$_6$, and R$_7$ bearing the substituent represent alkyl, alkenyl or alkynyl groups;
- an acetylamino group; a linear or branched C$_1$-C$_6$ alkoxy group; a linear or branched C$_1$-C$_6$ alkoxycarbonyl group; a hydroxycarbonyl group, a linear or branched C$_1$-C$_6$ alkoxycarbonyl group; a hydroxyl group; an amino group; a mono- or dialkylamino group; a mono- or dihydroxyalkylamino group, a nitro group, a halogen atom; and
- an aryl group, an aromatic or non-aromatic heterocycle, these cyclic groups being unsubstituted or substituted with the substituents mentioned above, or mesomeric forms thereof.

2. The process according to claim 1, wherein in formula (Ia), R$_1$ and R$_2$, independently of each other, are chosen from a hydrogen atom, a C$_1$-C$_6$ alkyl radical and a C$_1$-C$_6$ mono- or polyhydroxyalkyl radical.

3. The process according to claim 1, wherein in formula (Ia), R$_3$ is chosen from a hydrogen atom and an aryl radical, optionally substituted with an amino, dialkylamino or dihydroxyalkylamino group.

4. The process according to claim 1, wherein in formula (Ia), n is 1 and R$_5$ is the divalent group CR$_6$R$_7$, wherein R$_6$ and R$_7$ are each a C$_1$-C$_4$ alkyl, optionally substituted with at least one halogen atom.

5. The process according to claim 1, wherein the at least one triarylmethane-based direct dye of formula (Ia) is formed by a group chosen from the following:

[7-Dimethylamino-9,9-dimethyl-9H-anthracen-2-ylidene]dimethylammonium;

[7-Dimethylamino-10-ethyl-9,9-dimethyl-9H-anthracen-2-ylidene]-dimethylammonium;

[7-Dimethylamino-10-(4-dimethylaminophenyl)-9,9-dimethyl-9H-anthracen-2-ylidene]dimethylammonium;

[7-Diethylamino-10-(4-diethylaminophenyl)-9,9-dimethyl-9H-anthracen-2-ylidene]dimethylammonium;

Methanaminium, N-[6-(dimethylamino)-9-(1-naphthalenyl)-3 H-fluoren-3-ylidene]-N-methyl;

Methanaminium, N-[6-(dimethylamino)-9-(4-pyridyl)-3H-fluoren-3-ylidene]-N-methyl;

Methanaminium, N-[9-[4-(dimethylamino)phenyl]-3H-fluoren-3-ylidene]-N-methyl;

Bis [3,6-bis(dimethylamino)-9-phenylfluoren-9-ylium];

Benzoic acid, 2-[3,6-bis(dimethylamino)-9H-fluoren-9-ylium];

3,6-Bis(dimethylamino)-9-(p-methoxyphenyl)fluoren-9-ylium;

4-(3,6-Diaminofluoren-9-ylidene)cyclohexa-2,5-dienylideneammonium;

[4-(3,6-Bis-aminofluoren-9-ylidene)-2-rnethylcyclohexa-2,5-dienylidene]ammonium;

[4-(3,6-Bis-amino-2,7-dichlorofluoren-9-ylidene)cyclohexa-2,5-dielenylidene]ammonium;

9H-Fluorene-3,6-diamine, N,N'-dimethyl-9-[4-(methylamino)-phenyl]; [4-(3,6-Bis-dimethylaminofluoren-9-ylidene)cyclohexa-2,5-dienylidene]methylammonium;

[4-(3,6-Bis-dimethylaminofluoren-9-ylidene)cyclohexa-2,5-dienylidene]dimethylammonium;

[4-(3,6-Bis-diethylaminofluoren-9-ylidene)cyclohexa-2,5-dienylidene]diethyiammonium;

Ethanaminium, N-[9-[2,6-dichloro-4-(diethylamino)phenyl]-6-(diethylamino)-2,7-dimethyl-3H-fluoren-3-ylidene]-N-ethyl;

Ethanaminium, N-[6-(diethylamino)-9-[4-(diethylamino)-2-nitrophenyl]-2,7-bis(1,1-dimethylethyl)-3H-fluoren-3-ylidene]-N-ethyl;

Ethanaminium, N-[9-[2-butyl-4-(diethylamino)phenyl]-6-(diethyl-amino)-3H-fluoren-3-ylidene]-N-ethyl;

Benzoic acid, 2-[3,6-bis(diethylamino)-9H-fluoren-9-yl]-5-(dimethylamino);

Benzoic acid, 2-[3-(diethylamino)-6-(dimethylamino)-9H-fluoren-9-yl]-5-(dimethylamino);

Phenol, 2-[3-[3,6-bis(dimethylamino)-9H-fluoren-9-ylidene]-3H-indol-2-yl];

Methanaminium, N-[6-(dimethylamino)-9-[(4-nitrophenyl)ethynyl]-3H-fluoren-3-ylidene]-N-methyl;

Methanaminium, N-[9-[(4-bromophenyl)ethynyl]-6-(dimethylamino)-3H-fluoren-3-ylidene]-N-methyl;

Methanaminium, N-[6-(dimethylamino)-9-(phenylethynyl)-3H-fluoren-3-ylidene]-N-methyl;

Methanaminium, N-[6-(dimethylamino)-9-[(4-methylphenyl)-ethynyl]-3H-fluoren-3-ylidene]-N-methyl;

Methanaminium, N-[6-(dimethylamino)-9-[(4-methoxyphenyl)-ethynyl]-3H-fluoren-3-ylidene]-N-methyl;

Methanaminium, N-[6-(dimethylamino)-9-[4-(dimethylamino)-phenyl]ethynylj-3H-fluoren-3-ylidene]-N-methyl; and 9H-Fluorene-3,6-diamine, 9-(4-pyridylmethylene).

6. The process according to claim 1, wherein the at least one triarylmethane-based dye of formula (Ia) is present in the dye composition in an amount ranging from 0.001% to 20% based on the total weight of the composition.

7. The process according to claim 6, wherein the at least one triarylmethane-based dye of formula (Ia) is present in the dye composition in an amount ranging from 0.01% to 10% based on the total weight of the composition.

8. The process according to claim 7, wherein the at least one triarylmethane-based dye of formula (Ia) is present in the dye composition in an amount ranging from 0.1% to 5% based on the total weight of the composition.

9. The process according to claim 1, wherein the process further comprises leaving the cosmetic composition on the fibers for a period ranging from 3 minutes to one hour and then rinsing the composition from the keratin fibers.

10. The process according to claim 9, wherein the cosmetic composition is left on the fibers for a period ranging from 15 to 45 minutes.

11. A direct dye composition for dyeing keratin fibers comprising:

a medium suitable for dyeing and at least one direct dye chosen from a triarylmethane-based compound of formula (Ia), contained in said medium:

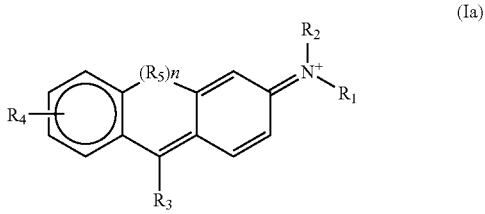

in which:

R₁, R₂ and R₃ are, independently of each other, chosen from a hydrogen atom, a linear or branched, substituted or unsubstituted $C_1$-$C_{24}$ alkyl or $C_2$-$C_{24}$ alkenyl or alkynyl radical, a substituted or unsubstituted benzyl radical, a substituted or unsubstituted aryl radical or an aromatic or nonaromatic, and a substituted or unsubstituted heterocycle radical;

R₄ is chosen from a hydrogen atom and a substituted or unsubstituted amino group;

R₅ is a group —CR₆R₇— in which R₆ and R₇ are, independently of each other, chosen from a hydrogen atom, a linear or branched, substituted or unsubstituted $C_1$-$C_{24}$ alkyl radical, which can cyclize, a substituted or unsubstituted benzyl radical or and a substituted or unsubstituted aryl radical;

n is chosen from 0 and 1; and the dye of formula (Ia) optionally having at least one other substituent, a radical being said to be substituted when it bears at least one group chosen from:

- a linear or branched $C_1$-$C_6$ alkyl group, except when the groups R₁, R₂, R₃, R₆, and/or R₇ bearing the substituent represent alkyl, alkenyl or alkynyl groups;
- a linear or branched $C_1$-$C_6$ hydroxyalkyl group, except when the groups R₁, R₂, R₃, R₆, and R₇ bearing the substituent represent alkyl, alkenyl or alkynyl groups;
- an acetylamino group; a linear or branched $C_1$-$C_6$ alkoxy group; a linear or branched $C_1$-$C_6$ alkoxycarbonyl group; a hydroxycarbonyl group, a linear or branched $C_1$-$C_6$ alkoxycarbonyl group; a hydroxyl group; an amino group; a mono- or dialkylamino group; a mono- or dihydroxyalkylamino group, a nitro group, a halogen atom; and
  - an aryl group, an aromatic or non-aromatic heterocycle, these cyclic groups being unsubstituted or substituted with the substituents mentioned above, or mesomeric forms thereof.

12. The dye composition according to claim 11, wherein in formula (Ia), R₁ and R₂, independently of each other, are chosen from a hydrogen atom, a $C_1$-$C_6$ alkyl radical and a $C_1$-$C_6$ mono- or polyhydroxyalkyl radical.

13. The dye composition according to claim 11, wherein in formula (Ia), R₃ is chosen from a hydrogen atom and an aryl radical, optionally substituted with an amino, dialkylamino or dihydroxyalkylamino group.

14. The dye composition according to claim 11, wherein in formula (Ia), n is 1 and R₅ is the divalent group CR₆R₇, wherein R₆ and R₇ are each a $C_1$-$C_4$ alkyl, optionally substituted with at least one halogen atom.

15. The dye composition according to claim 11, wherein the at least one triarylmethane-based direct dye of formula (Ia) is formed by a group chosen from the following:

[7-Dimethylamino-9,9-dimethyl-9H-anthracen-2-ylidene]dimethylammonium;

[7-Dimethylamino-10-ethyl-9,9-dimethyl-9H-anthracen-2-ylidene]-dimethylammonium;

[7-Dimethylamino-10-(4-dimethylaminophenyl)-9,9-dimethyl-9H-anthracen-2-ylidene]dimethylammonium;

[7-Diethylamino-10-(4-diethylaminophenyl)-9,9-dimethyl-9H-anthracen-2-ylidene]dimethylammonium;

Methanaminium, N-[6-(dimethylamino)-9-(1-naphthalenyl)-3H-fluoren-3-ylidene]-N-methyl;

Methanaminium, N-[6-(dimethylamino)-9-(4-pyridyl)-3H-fluoren-3-ylidene]-N-methyl;

Methanaminium, N-[9-[4-(dimethylamino)phenyl]-3H-fluoren-3-ylidene]-N-methyl;

Bis [3,6-bis(dimethylamino)-9-phenylfluoren-9-ylium];

Benzoic acid, 2-[3,6-bis(dimethylamino)-9H-fluoren-9-ylium];

3,6-Bis(dimethylamino)-9-(p-methoxyphenyl)fluoren-9-ylium;

4-(3,6-Diaminofluoren-9-ylidene)cyclohexa-2,5-dienylideneammonium;

[4-(3,6-Bis-aminofluoren-9-ylidene)-2-rnethylcyclohexa-2,5-dienylidene]ammonium;

[4-(3,6-Bis-amino-2,7-dichlorofluoren-9-ylidene)cyclohexa-2, 5-dienylidene]ammonium;

9H-Fluorene-3,6-diamine, N,N'-dimethyl-9-[4-(methylamino)- phenyl];

[4-(3,6-Bis-dimethylaminofluoren-9-ylidene)cyciohexa-2,5-dienylidene]methylammonium;

[4-(3,6-Bis-dimethylaminofluoren-9-ylidene)cyclohexa-2,5-dienylidene]dimethylammonium;

[4-(3,6-Bis-diethylaminofluoren-9-ylidene)cyclohexa-2, 5-dienylidene]diethylammonium;

Ethanaminium, N-[9-[2,6-dichloro-4-(diethylamino)phenyl]-6-(diethylamino)-2,7-dimethyl-3H-fluoren-3-ylidene]-N-ethyl;

Ethanaminium, N-[6-(diethylamino)-9-[4-(diethylamino)-2-nitrophenyl]-2,7-bis (1,1-dimethylethyl)-3H-fluoren-3-ylidene]-N-ethyl;

Ethanaminium, N-[9-[2-butyl-4-(diethylamino)phenyl]-6-(diethylamino)-3H-fluoren-3-ylidene]-N-ethyl;

Benzoic acid, 2-[3,6-bis(diethylamino)-9H-fluoren-9-yl]-5-(dimethylamino);

Benzoic acid, 2-[3-(diethylamino)-6-(dimethylamino)-9H-fluoren-9-yl]-5-(dimethylamino);

Phenol, 2-[3-[3,6-bis(dimethylamino)-9H-fluoren-9-ylidene]-3H-indol-2-yl];

Methanaminium, N-[6-(dimethylamino)-9-[(4-nitrophenyl)ethynyl]-3H-fluoren-3-ylidene]-N-methyl;

Methanaminium, N-[9-[(4-bromophenyl)ethynyl]-6-(dimethylamino)-3H-fluoren-3-ylidene]-N-methyl;

Methanaminium, N-[6-(dimethylamino)-9-(phenylethynyl)-3H-fluoren-3-ylidene]-N-methyl;

Methanaminium, N-[6-(dimethylamino)-9-[(4-methylphenyl)-ethynyl]-3H-fluoren-3-ylidene]-N-methyl;

Methanaminium, N-[6-(dimethylamino)-9-[(4-methoxyphenyl)-ethynyl]-3H-fluoren-3-ylidene]-N-methyl;

Methanaminium, N-[6-(dimethylamino)-9-[4-(dimethylamino)-phenyl]ethynylj-3H-fluoren-3-ylidene]-N-methyl; and 9H-Fluorene-3,6-diamine, 9-(4-pyridylmethylene).

16. The dye composition according to claim 11, wherein the at least one triarylmethane-based dye of formula (Ia) is present in the dye composition in an amount ranging from 0.001% to 20% based on the total weight of the composition.

17. The dye composition according to claim 11, wherein the at least one triarylmethane-based dye of formula (Ia) is present in the dye composition in an amount ranging from 0.01% to 10% based on the total weight of the composition.

18. The dye composition according to claim 11, wherein the at least one triarylmethane-based dye of formula (Ia) is present in the dye composition in an amount ranging from 0.1% to 5% based on the total weight of the composition.

19. An aqueous dye composition for dyeing keratin fibers, comprising:
a medium suitable for dyeing;
at least one direct dye chosen from a triarylmethane-based compound of formula (Ia), contained in said medium,

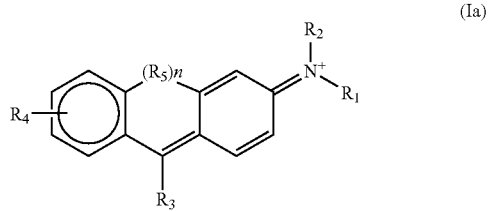

in which:
$R_1$, $R_2$ and $R_3$ are, independently of each other, chosen from a hydrogen atom, a linear or branched, substituted or unsubstituted $C_1$-$C_{24}$ alkyl or $C_2$-$C_{24}$ alkenyl or alkynyl radical, a substituted or unsubstituted benzyl radical, a substituted or unsubstituted aryl radical or an aromatic or nonaromatic, and a substituted or unsubstituted heterocycle radical;
$R_4$ is chosen from a hydrogen atom and a substituted or unsubstituted amino group;
$R_5$ is a group —$CR_6R_7$— in which $R_6$ and $R_7$ are, independently of each other, chosen from a hydrogen atom, a linear or branched, substituted or unsubstituted $C_1$-$C_{24}$ alkyl radical, which can cyclize, a substituted or unsubstituted benzyl radical and a substituted or unsubstituted aryl radical;
n is chosen from 0 and 1; and
the dye of formula (Ia) optionally having at least one other substituent, a radical being said to be substituted when it bears at least one group chosen from:
  a linear or branched $C_1$-$C_6$ alkyl group, except when the groups $R_1$, $R_2$, $R_3$, $R_6$, and/or $R_7$ bearing the substituent represent alkyl, alkenyl or alkynyl groups;
  a linear or branched $C_1$-$C_6$ hydroxyalkyl group, except when the groups $R_1$, $R_2$, $R_3$, $R_6$, and $R_7$ bearing the substituent represent alkyl, alkenyl or alkynyl groups;
  an acetylamino group; a linear or branched $C_1$-$C_6$ alkoxy group; a linear or branched $C_1$-$C_6$ alkoxycarbonyl group; a hydroxycarbonyl group, a linear or branched $C_1$-$C_6$ alkoxycarbonyl group; a hydroxyl group; an amino group; a mono- or dialkylamino group; a mono- or dihydroxyalkylamino group, a nitro group, a halogen atom; and
  an aryl group, an aromatic or non-aromatic heterocycle, these cyclic groups being unsubstituted or substituted with the substituents mentioned above, or mesomeric forms thereof;
at least one oxidation base; and/or
at least one direct dye other than the triarylmethane-based dye of formula (Ia).

20. The dye composition according to claim 19, wherein the at least one triarylmethane-based dye of formula (Ia) is present in the dye composition in an amount ranging from 0.001% to 20% by weight based on the total weight of the dye composition.

21. The dye composition according to claim 20, wherein the at least triarylmethane-based direct dye of formula (Ia) is present in the dye composition in an amount ranging from 0.01% to 10% by weight based on the total weight of the dye composition.

22. The dye composition according to claim 19, wherein the at least one oxidation base is chosen from para-phenylenediamines, bis(phenyl)alkylenediamines, para-aminophenols, ortho-aminophenols and heterocyclic bases, and addition salts thereof.

23. The dye composition according to claim 22, wherein the at least one oxidation base is present in an amount ranging from 0.001% to 20% by weight based on the total weight of the dye composition.

24. The dye composition according to claim 23, wherein the at least one oxidation base is present in an amount ranging from 0.005% to 6% by weight based on the total weight of the dye composition.

25. The dye composition according to claim 19, further comprising at least one additional direct dye other than the at least one triarylmethane-based dye of formula (Ia), wherein the at least one additional direct dye is chosen from neutral, acidic or cationic nitrobenzene dyes, neutral, acidic or cationic azo direct dyes, neutral, acidic, or cationic quinone, azine direct dyes, triarylmethane direct dyes, indoamine direct dyes and natural direct dyes.

26. The dye composition according to claim 25, wherein the at least one additional direct dye is present in an amount ranging from 0.001% to 20% by weight based on the total weight of the dye composition.

27. The dye composition according to claim 26, wherein the at least one additional direct dye is present in an amount ranging from 0.005% to 10% by weight based on the total weight of the dye composition.

28. The dye composition according to claim 19, further comprising at least one coupler chosen from metaphenylenediamines, meta-aminophenols, meta-diphenols, naphthalene-based couplers and heterocyclic couplers, and addition salts thereof.

29. The dye composition according to claim 28, wherein the at least one coupler is chosen from 1,3-dihydroxybenzene, 1,3-dihydroxy-2-methylbenzene, 4-chloro-1,3-dihydroxybenzene, 2,4-diamino-1-(β-hydroxyethyloxy)-benzene, 2-amino-4-(β-hydroxyethylamino)-1-methoxybenzene, 1,3-diaminoenzene, 1,3-bis(2,4-diaminophenoxy)propane, 3-ureidoaniline, 3-ureido-1-dimethylaminobenzene, sesamol, 1-βhydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylene-dioxybenzene and 2,6-bis (β-hydroxyethylamino)toluene, and addition salts thereof.

30. The dye composition according to claim 28, wherein the at least one coupler is present in an amount ranging from 0.001% to 20% by weight based on the total weight of the dye composition.

31. The dye composition according to claim 30, wherein the at least one coupler is present in an amount ranging from 0.005% to 6% by weight based on the total weight of the dye composition.

32. The dye composition according to claim 19, further comprising at least one oxidizing agent.

33. The dye composition according to claim 32, wherein the at least one oxidizing agent is chosen from hydrogen peroxide, urea peroxide, alkali metal bromates, persalts, peracids and oxidase enzymes.

34. The dye composition according to claim 32, wherein the at least one oxidizing agent is hydrogen peroxide.

35. The dye composition according to claim 19, further comprising at least one hydroxylated solvent.

36. The dye composition according to claim 35, wherein the at least one hydroxylated solvent is chosen from ethanol, propylene gylcol, glycerol and polyol monoethers.

37. The dye composition according to claim 19, further comprising at least one adjuvant.

38. The dye composition according to claim 37, wherein the at least one adjuvant is chosen from anionic, nonionic, amphoteric or zwitterionic surfactants or mixtures thereof, anionic, cationic, nonionic, amphoteric or zwitterionic polymers or mixtures thereof, anionic, cationic, nonionic and amphoteric associative thickeners, antioxidants, penetrating agents, sequestering agents, fragrances, buffers, dispersants, volatile or non-volatile, modified or unmodified silicones, film-forming agents, ceramides, preserving agents and opacifiers.

39. A process for lightening keratin fibers comprising:
applying a cosmetic composition to keratin fibers, the cosmetic composition, free of an oxidizing agent and of an oxidation base, comprising a medium suitable for dyeing and a direct dye of formula (Ia), contained in said medium,

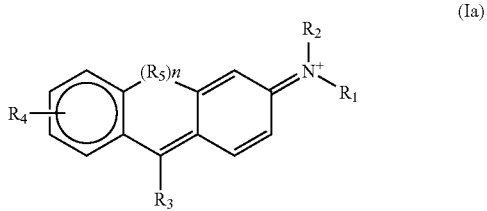

in which:
$R_1$, $R_2$ and $R_3$, are, independently of each other, chosen from a hydrogen atom, a linear or branched, substituted or unsubstituted $C_1$-$C_{24}$ alkyl or $C_2$-$C_{24}$ alkenyl or alkynyl radical, a substituted or unsubstituted benzyl radical, a substituted or unsubstituted aryl radical or an aromatic or nonaromatic, and a substituted or unsubstituted heterocycle radical;

$R_4$ is chosen from a hydrogen atom and a substituted or unsubstituted amino group;

$R_5$ is a group —$CR_6R_7$— in which $R_6$ and $R_7$ are, independently of each other, chosen from a hydrogen atom, a linear or branched, substituted or unsubstituted $C_1$-$C_{24}$ alkyl radical, which can cyclize, a substituted or unsubstituted benzyl radical and a substituted or unsubstituted aryl radical;

n is chosen from 0 and 1; and the dye of formula (Ia) optionally having at least one other substituent, a radical being said to be substituted when it bears at least one group chosen from:
a linear or branched $C_1$-$C_6$ alkyl group, except when the groups $R_1$, $R_2$, $R_3$, $R_6$, and/or $R_7$ bearing the substituent represent alkyl, alkenyl or alkynyl groups;
a linear or branched $C_1$-$C_6$ hydroxyalkyl group, except when the groups $R_1$, $R_2$, $R_3$, $R_6$, and $R_7$ bearing the substituent represent alkyl, alkenyl or alkynyl groups;
an acetylamino group; a linear or branched $C_1$-$C_6$ alkoxy group; a linear or branched $C_1$-$C_6$ alkoxycarbonyl group; a hydroxycarbonyl group, a linear or branched $C_1$-$C_6$ alkoxycarbonyl group; a hydroxyl group; an amino group; a mono- or dialkylamino group; a mono- or dihydroxyalkylamino group, a nitro group, a halogen atom; and an aryl group, an aromatic or non-aromatic heterocycle, these cyclic groups being unsubstituted or substituted with the substituents mentioned above, or mesomeric forms thereof;
applying an oxidizing composition to the keratin fibers simultaneously with or sequentially to the cosmetic composition;
leaving the cosmetic composition and the oxidizing composition on the fibers for a period of time ranging from 3 minutes to 1 hour; and
then rinsing the fibers, shampooing the fibers, rinsing the fibers and then drying the fibers.

40. The process according to claim 39, wherein the cosmetic composition and the oxidizing composition are left on the fibers for a period of time ranging from 15 to 45 minutes.

41. A process for dyeing keratin fibers comprising
applying a cosmetic composition to keratin fibers, the cosmetic composition, free of an oxidizing agent, comprising a medium suitable for dyeing and a direct dye of formula (Ia), contained in said medium,

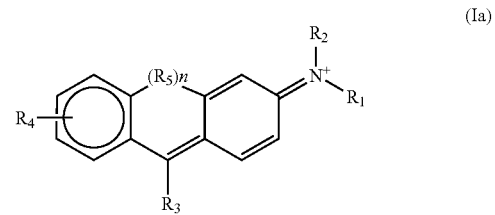

in which:
$R_1$, $R_2$ and $R_3$, are, independently of each other, chosen from a hydrogen atom, a linear or branched, substituted or unsubstituted $C_1$-$C_{24}$ alkyl or $C_2$-$C_{24}$ alkenyl or alkynyl radical, a substituted or unsubstituted benzyl radical, a substituted or unsubstituted aryl radical or an aromatic or nonaromatic, and a substituted or unsubstituted heterocycle radical;

$R_4$ is chosen from a hydrogen atom and a substituted or unsubstituted amino group;

$R_5$ is a group —$CR_6R_7$— in which $R_6$ and $R_7$ are, independently of each other, chosen from a hydrogen atom, a linear or branched, substituted or unsubstituted $C_1$-$C_{24}$ alkyl radical, which can cyclize, a substituted or unsubstituted benzyl radical and a substituted or unsubstituted aryl radical;

n is chosen from 0 and 1; and the dye of formula (Ia) optionally having at least one other substituent, a radical being said to be substituted when it bears at least one group chosen from:
a linear or branched $C_1$-$C_6$ alkyl group, except when the groups $R_1$, $R_2$, $R_3$, $R_6$, and/or $R_7$ bearing the substituent represent alkyl, alkenyl or alkynyl groups;
a linear or branched $C_1$-$C_6$ hydroxyalkyl group, except when the groups $R_1$, $R_2$, $R_3$, $R_6$, and $R_7$ bearing the substituent represent alkyl, alkenyl or alkynyl groups;
an acetylamino group; a linear or branched $C_1$-$C_6$ alkoxy group; a linear or branched $C_1$-$C_6$ alkoxycarbonyl group; a hydroxycarbonyl group, a linear or branched $C_1$-$C_6$ alkoxycarbonyl group; a hydroxyl group; an amino group; a mono- or dialkylamino group; a mono- or dihydroxyalkylamino group, a nitro group, a halogen atom; and an aryl group, an aromatic or non-aromatic heterocycle, these cyclic groups being unsubstituted or substituted with the substituents mentioned above, or mesomeric forms thereof;

applying an oxidizing composition to the keratin fibers simultaneously with, or sequentially to, the cosmetic composition, leaving the cosmetic composition and the oxidizing composition on the fibers for a period of time ranging from 3 minutes to 1 hour; and then rinsing the fibers, shampooing the fibers, rinsing the fibers and then drying the fibers.

42. The process according to claim 41, wherein the cosmetic composition and the oxidizing composition are left on the fibers for a period of time ranging from 15 to 45 minutes.

43. A multi-compartment device comprising:
a first compartment containing a direct dye composition, free of an oxidizing agent and oxidizing base, the direct dye composition comprising a medium suitable for dyeing and a direct dye of formula (Ia), contained in said medium,

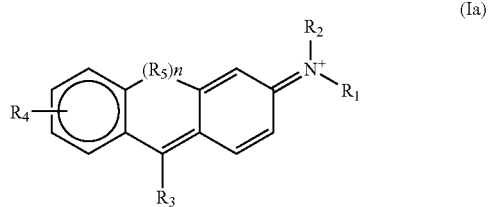
(Ia)

in which:
$R_1$, $R_2$ and $R_3$, are, independently of each other, chosen from a hydrogen atom, a linear or branched, substituted or unsubstituted $C_1$-$C_{24}$ alkyl or $C_2$-$C_{24}$ alkenyl or alkynyl radical, a substituted or unsubstituted benzyl radical, a substituted or unsubstituted aryl radical or an aromatic or nonaromatic, and a substituted or unsubstituted heterocycle radical;

$R_4$ is chosen from a hydrogen atom and a substituted or unsubstituted amino group;

$R_5$ is a group —$CR_6R_7$— in which $R_6$ and $R_7$ are, independently of each other, chosen from a hydrogen atom, a linear or branched, substituted or unsubstituted $C_1$-$C_{24}$ alkyl radical, which can cyclize, a substituted or unsubstituted benzyl radical and a substituted or unsubstituted aryl radical;

n is chosen from 0 and 1; and the dye of formula (Ia) optionally having at least one other substituent, a radical being said to be substituted when it bears at least one group chosen from:

a linear or branched $C_1$-$C_6$ alkyl group, except when the groups $R_1$, $R_2$, $R_3$, $R_6$, and/or $R_7$ bearing the substituent represent alkyl, alkenyl or alkynyl groups;

a linear or branched $C_1$-$C_6$ hydroxyalkyl group, except when the groups $R_1$, $R_2$, $R_3$, $R_6$, and $R_7$ bearing the substituent represent alkyl, alkenyl or alkynyl groups;

an acetylamino group; a linear or branched $C_1$-$C_6$ alkoxy group; a linear or branched $C_1$-$C_6$ alkoxycarbonyl group; a hydroxycarbonyl group, a linear or branched $C_1$-$C_6$ alkoxycarbonyl group; a hydroxyl group; an amino group; a mono- or dialkylamino group; a mono- or dihydroxyalkylamino group, a nitro group, a halogen atom; and an aryl group, an aromatic or non-aromatic heterocycle, these cyclic groups being unsubstituted or substituted with the substituents mentioned above, or mesomeric forms thereof; and a second compartment containing a composition comprising an oxidizing agent.

44. The device according to claim 43, wherein the first compartment comprises an oxidation dye precursor.

45. An aqueous dye composition for dyeing keratin fibers, comprising:
a medium suitable for dyeing;
at least one leuco compound of formula (Ib), contained in said medium,

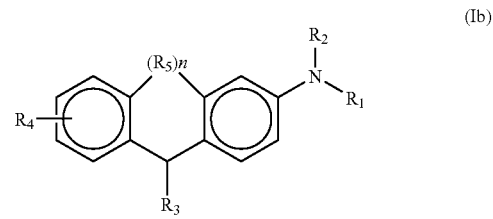
(Ib)

in which:
$R_1$, $R_2$ and $R_3$, which are, independently of each other, chosen from a hydrogen atom, a linear or branched, substituted or unsubstituted $C_1$-$C_{24}$ alkyl or $C_2$-$C_{24}$ alkenyl or alkynyl radical, a substituted or unsubstituted benzyl radical, a substituted or unsubstituted aryl radical or an aromatic or nonaromatic, and substituted or unsubstituted heterocycle radical;

$R_4$ is chosen from a hydrogen atom and a substituted or unsubstituted amino group;

$R_5$ is a group —$CR_6R_7$— in which $R_6$ and $R_7$, which are the same or different, are chosen from a hydrogen atom, a linear or branched, substituted or unsubstituted $C_1$-$C_{24}$ alkyl radical, which can cyclize, a substituted or unsubstituted benzyl radical and a substituted or unsubstituted aryl radical;

n chosen from 0 and 1;
at least one oxidation base; and/or
at least one additional dye.

46. A process for dyeing keratin fibers comprising:
applying a cosmetic composition, free of oxidizing agent, to keratin fibers, the cosmetic composition comprising an aqueous dye composition comprising,
a medium suitable for dyeing;
at least one leuco compound of formula (Ib), contained in said medium,

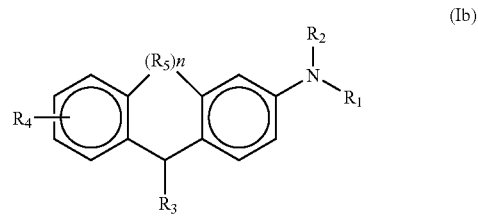
(Ib)

in which:
$R_1$, $R_2$ and $R_3$, which are, independently of each other, chosen from a hydrogen atom, a linear or branched, substituted or unsubstituted $C_1$-$C_{24}$ alkyl or $C_2$-$C_{24}$ alkenyl or alkynyl radical, a substituted or unsubstituted benzyl radical, a substituted or unsubstituted aryl radical or an aromatic or nonaromatic, and substituted or unsubstituted heterocycle radical;

$R_4$ is chosen from a hydrogen atom and a substituted or unsubstituted amino group;

$R_5$ is a group —$CR_6R_7$— in which $R_6$ and $R_7$, which are the same or different, are chosen from a hydrogen atom, a linear or branched, substituted or unsubstituted $C_1$-$C_{24}$ alkyl radical, which can cyclize, a substituted or unsubstituted benzyl radical and a substituted or unsubstituted aryl radical;

n chosen from 0 and 1;

at least one oxidation base; and/or at least one additional dye;

applying an oxidizing composition to the keratin fibers simultaneously with or sequentially to the cosmetic composition, leaving the cosmetic composition and the oxidizing composition on the fibers for a period of time ranging from 3 minutes to 1 hour; and then rinsing the fibers, washing the fibers with shampoo, rinsing the fibers again and drying the fibers.

47. The process according to claim 46, wherein the cosmetic composition and the oxidizing composition are left on the fibers for a period of time ranging from 15 to 45 minutes.

48. A multi-compartment device comprising:

a first compartment containing a composition, free of an oxidizing agent, the composition comprising an aqueous dye composition comprising, a medium suitable for dyeing;

at least one leuco compound of formula (Ib), contained in said medium,

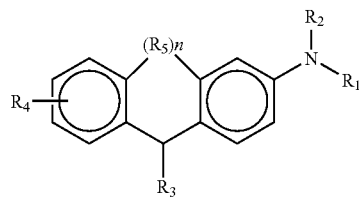

in which:

$R_1$, $R_2$ and $R_3$, which are, independently of each other, chosen from a hydrogen atom, a linear or branched, substituted or unsubstituted $C_1$-$C_{24}$ alkyl or $C_2$-$C_{24}$ alkenyl or alkynyl radical, a substituted or unsubstituted benzyl radical, a substituted or unsubstituted aryl radical or an aromatic or nonaromatic, and substituted or unsubstituted heterocycle radical;

$R_4$ is chosen from a hydrogen atom and a substituted or unsubstituted amino group;

$R_5$ is a group —$CR_6R_7$— in which $R_6$ and $R_7$, which are the same or different, are chosen from a hydrogen atom, a linear or branched, substituted or unsubstituted $C_1$-$C_{24}$ alkyl radical, which can cyclize, a substituted or unsubstituted benzyl radical and a substituted or unsubstituted aryl radical;

n chosen from 0 and 1;

at least one oxidation base; and/or at least one additional dye; and a second compartment containing a composition comprising an oxidizing agent.

* * * * *

UNITED STATES PATENT AND TRADEMARK OFFICE
CERTIFICATE OF CORRECTION

PATENT NO. : 7,329,289 B2  
APPLICATION NO. : 11/141204  
DATED : February 12, 2008  
INVENTOR(S) : Lagrange et al.

Page 1 of 1

It is certified that error appears in the above-identified patent and that said Letters Patent is hereby corrected as shown below:

Claim 5, col. 30, line 6, start new paragraph after the ";".

Claim 5, col. 30, line 38, "9-[4-" should read -- 9-[[4- --.

Claim 5, col. 30, line 39, "ethynylj" should read -- ethynyl] --.

Claim 15, col. 32, line 19, "2- rnethycyclohexa" should read -- 2-methylcyclohexa --.

Claim 15, col. 32, line 25, "cyciohexa" should read -- cyclohexa --.

Claim 15, col. 32, line 56, "9-[4-" should read -- 9-[[4- --.

Claim 15, col. 32, line 57, "ethynylj" should read -- ethynyl] --.

Claim 29, col. 34, line 46, insert dash between "β" and "hydroxyethylamino".

Signed and Sealed this

Third Day of June, 2008

JON W. DUDAS  
*Director of the United States Patent and Trademark Office*